United States Patent
Patel et al.

(10) Patent No.: US 11,810,135 B2
(45) Date of Patent: Nov. 7, 2023

(54) SYSTEM AND METHOD FOR GENERATING TRANSACTION TRIGGER DATA STRUCTURES FOR AGGREGATED REPORTING

(71) Applicant: Otsuka America Pharmaceutical, Inc., Rockville, MD (US)

(72) Inventors: Paresh Patel, Princeton, NJ (US); Nipa Parikh, Somerset, NJ (US); Jennifer Cichone, Asbury, NJ (US)

(73) Assignee: OTSUKA AMERICA PHARMACEUTICAL, INC., Rockville, MD (US)

( * ) Notice: Subject to any disclaimer, the term of this patent is extended or adjusted under 35 U.S.C. 154(b) by 0 days.

(21) Appl. No.: 16/912,661

(22) Filed: Jun. 25, 2020

(65) Prior Publication Data
US 2022/0156771 A1 May 19, 2022

Related U.S. Application Data

(60) Provisional application No. 62/866,529, filed on Jun. 25, 2019.

(51) Int. Cl.
*G06Q 30/00* (2023.01)
*G06Q 30/0203* (2023.01)
*G06F 16/955* (2019.01)

(52) U.S. Cl.
CPC ..... *G06Q 30/0203* (2013.01); *G06F 16/9558* (2019.01)

(58) Field of Classification Search
CPC ......... G06Q 30/0203; G06Q 10/06315; G06Q 10/06375; G06Q 10/06395; G06Q 10/00;
(Continued)

(56) References Cited

U.S. PATENT DOCUMENTS 7,571,171 B1 8/2009 Shaw
8,489,414 B2 7/2013 McEachern
(Continued)

OTHER PUBLICATIONS

Bog, Anja, Hasso Plattner, and Alexander Zeier. "A mixed transaction processing and operational reporting benchmark." Information Systems Frontiers 13.3 (2011): 321-335. (Year: 2011).*
(Continued)

*Primary Examiner* — Eric W Stamber
*Assistant Examiner* — Jay-Ming Wang
(74) *Attorney, Agent, or Firm* — Pillsbury Winthrop Shaw Pittman LLP

(57) ABSTRACT

Methods, systems, apparatus, and computer programs, for generating transaction trigger data structures for aggregated reporting. In one aspect, a method is disclosed that includes administering a survey that is automatically generated based on historical data, generating a transaction trigger data structure in a calendar application based on aggregated survey responses, the transaction trigger data structure including (i) a report identifier, (ii) a distribution list for the report, and (iii) triggering logic, detecting that the transaction trigger data structure is to be triggered, and executing the triggering logic of the at least one transaction trigger data structure, wherein execution of the transaction trigger record causing a computer to (i) generate a particular report type that is identified by the report identifier and (ii) distribute the report data structure to computers each respective recipient of the distribution list that is logically related to the report identifier for which the report was generated.

20 Claims, 3 Drawing Sheets

(58) Field of Classification Search
CPC ........ G06Q 10/02; G06Q 10/06; G06Q 10/10; G06Q 30/02; G06F 16/9558; G05B 2219/31357
See application file for complete search history.

(56) References Cited

U.S. PATENT DOCUMENTS

| | | | |
|---|---|---|---|
| 8,577,884 B2 | 11/2013 | Poteet et al. | |
| 8,983,972 B2 | 3/2015 | Kriebel et al. | |
| 9,015,073 B2 | 4/2015 | Mirra et al. | |
| 9,460,444 B2 | 10/2016 | Hao et al. | |
| 9,483,768 B2 | 11/2016 | Singh | |
| 2004/0093281 A1* | 5/2004 | Silverstein ............. | G06Q 20/04 705/26.8 |
| 2005/0202390 A1 | 9/2005 | Allen et al. | |
| 2006/0241988 A1* | 10/2006 | Yaskin ................... | G06Q 10/06 434/365 |
| 2006/0241992 A1* | 10/2006 | Yaskin ............... | G06Q 30/0204 705/7.36 |
| 2006/0241993 A1* | 10/2006 | Yaskin ............. | G06Q 10/06395 705/7.41 |
| 2006/0242004 A1* | 10/2006 | Yaskin ............... | G06Q 30/0203 705/7.38 |
| 2007/0288246 A1 | 12/2007 | Ebert | |
| 2009/0106371 A1 | 4/2009 | Schmidt-Karaca et al. | |
| 2009/0150217 A1* | 6/2009 | Luff ....................... | G06Q 30/02 705/14.67 |
| 2009/0327854 A1 | 12/2009 | Chhajer et al. | |
| 2011/0137808 A1 | 6/2011 | Meyer et al. | |
| 2015/0161632 A1* | 6/2015 | Humay .............. | G06Q 30/0203 705/7.32 |
| 2015/0178458 A1 | 6/2015 | Pellinat et al. | |
| 2016/0117383 A1* | 4/2016 | Patel ....................... | G06Q 50/01 707/738 |
| 2016/0117697 A1* | 4/2016 | Briere ................... | G06F 16/248 705/7.29 |
| 2016/0255139 A1* | 9/2016 | Rathod .............. | H04N 1/32101 709/203 |
| 2017/0049962 A1* | 2/2017 | Parikh .................... | G16H 20/17 |
| 2017/0339467 A1* | 11/2017 | Patel ................. | H04N 21/44227 |
| 2018/0239747 A1 | 8/2018 | Bills et al. | |

OTHER PUBLICATIONS

Qualtrics.com [online], "My Reports Basic Overview (360)," Nov. 22, 2017, retrieved on Sep. 29, 2020, retrieved from URL<https://www.qualtrics.com/support/employee-experience/creating-360-project/reports-tab-360/my-reports/my-reports-overview-360/>, 8 pages.

* cited by examiner

SYSTEM AND METHOD FOR GENERATING TRANSACTION TRIGGER DATA STRUCTURES FOR AGGREGATED REPORTING

CROSS-REFERENCE TO RELATED APPLICATIONS

This application claims the benefit of U.S. Provisional Patent Application No. 62/866,529 filed Jun. 25, 2019, the entire contents of which is incorporated herein by reference in its entirety.

BACKGROUND

Development of a drug can require the creation and submission of reports to health authorities in multiple different jurisdictions. Tracking deadlines related to these reports, creating these reports, submission of these reports, and follow-up related to these reports is an expensive and manually intense process.

SUMMARY

According to one innovative aspect of the present disclosure, a method for generating transaction trigger data structures for aggregated reporting is disclosed. In one aspect, the method can include actions of generating, by one or more computers, a survey based on historical data, distributing, by the one or more computers, a message that includes a reference to the survey to each computer of a plurality of computers, aggregating, by the one or more computers and using a data structure having fields structuring data corresponding to question-answer pairs of the survey, responses to the survey from each of the plurality of computers, generating, by the one or more computers, one or more transaction trigger data structures for inclusion in a calendar application based on the aggregated responses to the survey, wherein each transaction trigger data structure (i) is associated with a particular date and (ii) includes one or more fields structuring data that (a) indicates one or more report identifiers, (b) indicates, for each particular report identifier of the one or more report identifiers, a distribution list of one or more recipients that is logically related to the particular report identifier, and (c) includes triggering logic, and modifying, by the one or more computers, a date entry in a calendar application corresponding to the particular date to include the transaction trigger data structure.

Other versions include corresponding system apparatus, and computer programs to perform the actions of methods defined by instructions encoded on computer readable storage devices.

These and other versions may optionally include one or more of the following features. For instance, in some implementations, the method can further include subsequent to generation of the transaction trigger data structure and modification of the data entry in the calendar application: detecting, by the one or more computers and based on (i) data identifying a current date and (ii) the transaction trigger data structure stored in the calendar application, that the transaction trigger data structure is to be triggered, and executing, by the one or more computers, the triggering logic of the transaction trigger data structure, wherein execution of the triggering logic of the transaction trigger record causes the computer to: for each report identifier of the transaction trigger record: generating, by the one or more computers, a report data structure that includes fields structuring data representing a particular report type that is identified by the report identifier, and distributing, by the one or more computers, the report data structure to a computer that is associated with each recipient of the distribution list that is logically related to the report identifier for which the report was generated.

In some implementations, the generated survey can include a web form that is accessible via one or more networks.

In some implementations, the reference to the survey can include a hyperlink.

In some implementations, the triggering logic can include a computer programmed code that, when executed, causes a computer to: for each report identifier of the transaction trigger record: generate, by the one or more computers, a report data structure that includes fields structuring data representing a particular report type that is identified by the report identifier, and distributing, by the one or more computers, the report data structure to a computer that is associated with each recipient of the distribution list that is logically related to the report identifier for which the report was generated.

In some implementations, data identifying the triggering logic includes computer executable program code that causes the computer to perform the operations of (i) generating the report data structure and (ii) distributing the report data structure.

In some implementations, data identifying the triggering logic includes a reference to a memory location storing the computer executable program code that causes the computer to perform the operations of (i) generating the report data structure and (ii) distributing the report data structure.

In some implementations, executing the triggering logic of the transaction trigger data structure can include obtaining the computer executable program code that causes the computer to perform the operations of (i) generating the report data structure and (ii) distributing the report data structure.

In some implementations, the method can further include determining, by the one or more computers, a difference between (i) data identifying a current date and (ii) data describing a date of a calendar entry that has been modified to include a second transaction trigger record, and based on determining that the determined difference satisfies a predetermined threshold: for each second report identifier of the second transaction trigger record: distributing a message that includes a reminder related to a report identified by the second report identifier to each recipient of a distribution list that is logically related to the second report identifier.

DETAILED DESCRIPTION

The present disclosure relates to methods, systems, and computer programs for generating and using a transaction trigger record for aggregated reporting. The transaction trigger record can be dynamically generated, by a computing system, to define and trigger report generation based on results of dynamically administered surveys without user interaction in survey administration or report generation. The transaction trigger record, and associated, processes described herein, facilitate data aggregation and report generation tasks in a manner that is more efficient than conventional methods. For example, conventionally, teams of human users would be required to administer surveys, review results, and manual generation of reports. Such manual processes requires not only human capital, but also computing resources, as each of the human users are using different computing devices that each consume resources such processing power, memory, storage, etc. Such human users consume more resources than just those resources required to implemented the task—it also comes with additional human use resource consumption such as web browsing, music streaming, video stream, or a combination thereof. Thus, use of the present disclosure can result in a significant reduction in computer resources required by an enterprise.

Advantages of the present disclosure are achieved can be achieved using the calendar application programming interface (API). The calendar API enables an application server of the present disclosure that administers surveys, aggregates results of the surveys, and generates transaction trigger records to interface and update a personal calendar application. The personal calendar application can be installed and run on user device such as a smartphone. Alternatively, or in addition, the calendar application may be a cloud-based calendar application hosted by a cloud-based server that is accessible by the user device. The transaction trigger record, when triggered, can automatically cause generation of a report described by the transaction trigger record. Though certain implementations of the present disclosure facilitate adding the transaction trigger record to a personal calendar application, the present disclosure is not so limited. Instead, in come implementations, the generated transaction trigger record can be added to any calendar application using the calendar API module.

Figure 1:
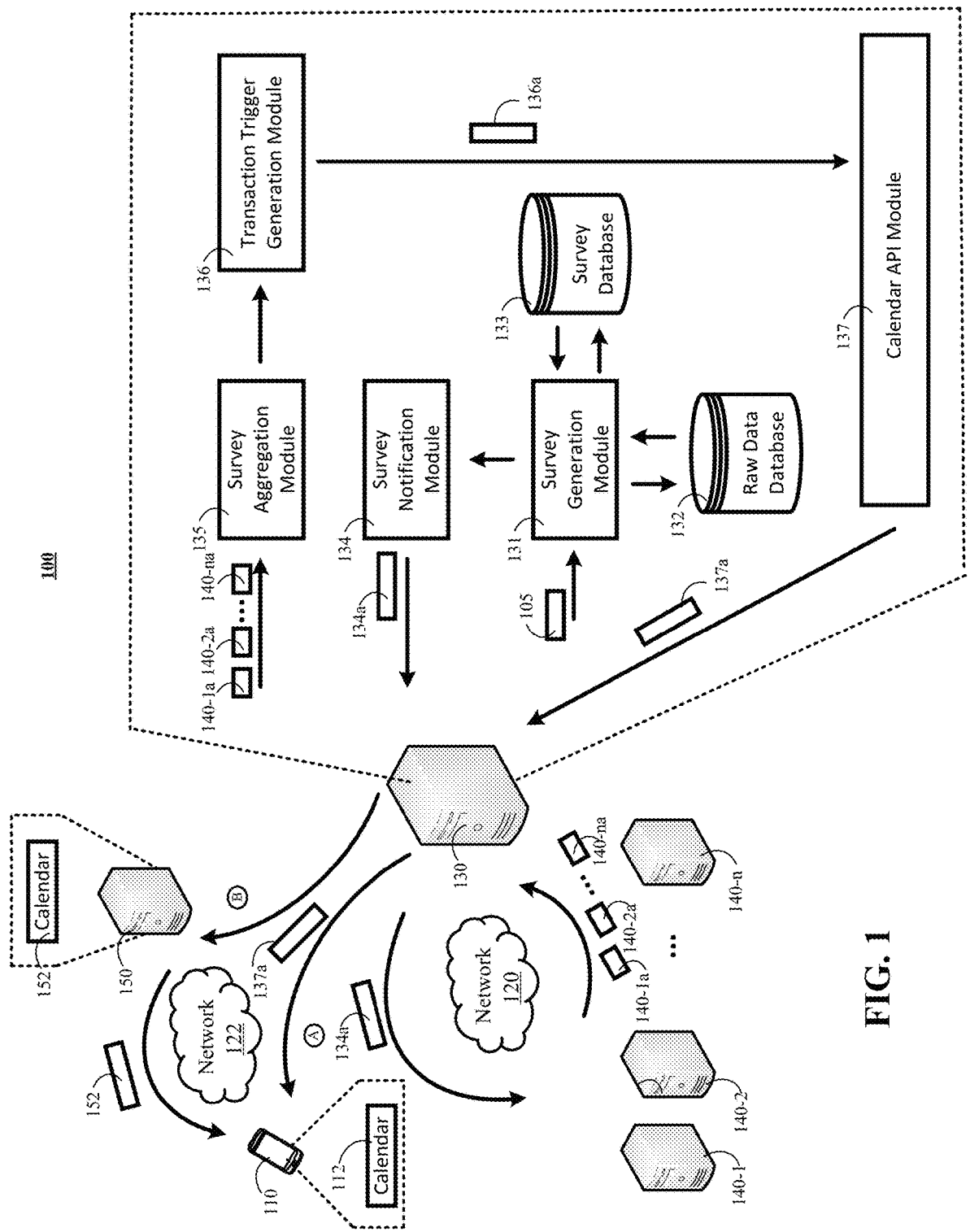
FIG. 1 is a block diagram of an example of a system for generating transaction trigger data structures for aggregated reporting.

FIG. 1 is a block diagram of an example of a system 100 for generating transaction trigger data structures for aggregated reporting. The system 100 can include a user device 110, one or more networks 120, 122, an application server 130, and one or more survey recipient computers 140-1, 140-2, 140-$n$. In some implementations, the system 100 can also include a computer 150 hosting a calendar application remotely from the user device 110. In some implementations, the computer 150 may be a cloud-based server. However, the present disclosure need not be so limited. For example, the computer 150 can be any computer on any network that hosts a calendar application remotely from a user device 110.

In the example of FIG. 1, the application server 130 can initiate generation of a survey using the survey generation module 131. The application server 130 can perform this action in response to an instruction 105 received by the survey generation module 131. The instruction 105 received by the survey generation module 131, and which instructs the survey generation module 131 to generate a survey, can be originated by one of multiple different sources, which is dependent on a particular implementation. In some implementations, for example, the instruction 105 can be generated and provided by the user device 110. In other implementations, the instruction 105 can be generated and provided by one of the computers 140-1. In other implementations, the instruction 105 can be generated and provided by the application server 130, itself.

In some implementations, the instruction 150 can be generated without user interaction. For example, the user device 110, the application server 130, or one of the computers 140-1, 140-2, 140-$n$, can generate and provide the instruction 105 based on processing of one or more business rules defining one or more types of criteria that need to be satisfied to trigger survey generation by the survey generation module 131. Likewise, in some implementations, the user device 110, the application server 130, or one of the computers 140-1, 140-2, 140-$n$ can be configured to periodically generate and provide the instructions 105 to the survey generation module 131 that instructions the survey generation module 131 to initiate generation of a survey. In some implementations, the user device 110, the application server 130, or one of the computers 140-1, 140-2, 140-$n$ can generate and provide the instruction 105 based on a determination that data stored in the raw data database 132 has exceeded a threshold amount of data storage, a determination that data stored in the raw data database 132 has exceeded a predetermined age, or the like. In other implementations, a human user of one of the user device 110, the application server 130, or one of the computers 140-1, 140-2, 140-$n$ can input instruction 105.

Responsive to receipt of the instruction 105, the survey generation module 131 can generate a survey using data stored in the raw data database 132. In some implementations, the raw data database 132 can store historical data that has been acquired by the application server 130. In some implementations, the historical data can include data generated during the course of a clinical trial, historical data generated to the development or marketing or sale of a drug or other product, historical data related to the safety of a particular drug or other product, or a combination thereof. The survey generation module 131 can access the raw data database 132 and generate survey questions generated based on data contained in the raw data database 132. In some implementations, the survey generation module 131 can obtain a survey template and use data stored in the raw data database 132 to populate the survey template. The survey generation module 131 can store the generated survey in the survey database 133. In some instances, after generation of the survey is complete, the survey generation module 131 can notify the survey notification module 134 that generation of the survey is complete. In some implementations, this can be achieved by the survey generation module 131 directly communicating with the survey notification module 134. In other implementations, this can be achieved indirectly by, for example, the survey generation module 131 toggling a flag indicating that generation of a survey is complete. In some implementations, the particular flag toggled by the survey generation unit 131 may correspond to a particular survey.

The survey notification module 134 can be configured to notify survey recipients such as computers 140-1, 140-2, 140-$n$, where n is any non-zero integer greater than 1, that a survey is ready for their review and completion. In some implementations, the survey notification module 134 can notify the computers 140-1, 140-2, 140-$n$ by generating an electronic message 134$a$ and distributing the generated message to each of the computers 140-1, 140-2, 140-$n$. Distributing the message 134$a$ can include, for example, transmitting the message 134$a$ to each of the computers 140-1, 140-2, 140-$n$ using the network 120. The network 120 can include an wired Ethernet network, a wireless WiFi network, an optical network, a LAN, a WAN, a cellular network, the Internet, or any combination thereof.

The electronic message 134a can include any electronic message including, for example, an email, a text message, a push message, an iOS notification, an Android notification, or the like. In some implementations, the electronic message 134a can include a link that, when selected by a user or artificially intelligent software/hardware agent associated with one of the computers 140-1, 140-2, 140-n, causes the computer 140-1, 140-2, or 140-n to access and display the generated survey data. The user or artificially intelligent software/hardware agent of each of the computers 140-1, 140-2, 140-n can then complete the generated survey.

The survey notification module 134 can monitor responses to distributed surveys and track the computers 140-1, 140-2, 140-n that have provided a response to the survey and those that have not provided a response to the survey. For example, in some implementations, the survey notification module 134 can maintain a response data structure such as an array, vector, or multi-column matrix of flags, with each flag corresponding to one of the computers 140-1, 140-2, 140-m. Upon distributing the surveys, the survey notification module 134 can initialize the flags of the data structure to a first state such as "0." Each survey response can include data identifying the computer that was used to complete the survey. Then, as the application server 130 receives responses 140-1a, 140-2a, 140-na, the survey notification module 134 can detect receipt of the survey responses and toggle a bit of the response data structure by, for example, changing a "0" to a "1" for each computer that has provided a response to the survey. Though the survey notification module 134 is described as maintaining the response data structure, the present disclosure need not be so limited. For example, other modules of the application server 130 can an alternative generate, update, track, and maintain the response data structure. For example, in some implementations, the response data structure can also be accessible to the survey aggregation module 135.

The survey notification module 134 can follow-up with one or more the computers 140-1, 140-2, 140-n, or users thereof, that have not provided a responses to the survey. In some implementations, for example, the survey notification module 134 can periodically send reminder messages to those computers that have not yet provided a response to the survey identified by 134a. In other messages, the survey notification module 134 may be programmed to send reminders to the one or more computers, based on the response data structure in accordance with one or more specific rules. For example, the survey notification module 134 can be programmed to send reminders at 15 days before the survey deadline, 10 days before the survey deadline, one week before the survey deadline, 2 days before the survey deadline, and day of the survey deadline.

The application server 130 can receive responses 140-1a, 140-2a, 140-na to the survey identified in the electronic message 134a. Upon completion of the survey, each computer 140-01, 140-2, 140-n can transmit a respective survey response 140-1a, 140-12a, 140-na that includes data identifying the transmitting computer, data identifying the destination computer, data indicating the survey to which the response corresponds, and data indicating answers to the questions of the survey input by the user or artificially intelligent software. The received response 140-1a, 140-2a, 140-na can be provided as inputs to the survey aggregation module 135.

The survey aggregation module 135 can obtain and aggregate the survey responses 140-1a, 140-2a, 140-na. For example, the survey aggregation module 135 can filter incoming survey responses 140-1a, 140-2a, 140-na into clusters based on a survey identifier, or other data indicating the survey to which the survey response corresponds, that is included within the survey response 140-1a, 140-2a, 140-na. Such a step can be needed because, in some implementations, there may multiple outstanding surveys at any given time. As a result, though only one survey is described as being distributed using electronic message 134a, multiple surveys may be distributed at any particular time, and responses to each of these different surveys may be received by the application server 130 and then aggregated, filtered, and clustered by the survey aggregation module 135.

In some implementations, the survey aggregation module 325 can monitor a response data structure for each distributed survey and determine, based on the response data structure, when a satisfactory amount of responses have been received. In some implementations, a satisfactory amount of responses can include receipt of a response from each computer to which the survey was distributed. Alternatively, in other implementations, a satisfactory amount of responses can include receipt of more than a threshold amount of response, falling below a threshold level of non-responses, or the like. Alternatively, in other implementations, a satisfactory amount of responses can include a number of responses received by a survey deadline. In some implementations, the survey aggregation module 325 need not monitor the response data structure. Instead, in such implementations, another modules such as the survey notification module 134 can monitor the response data structure and then provide instructions to the survey aggregation module 135 when a satisfactory amount of responses have been received.

The transaction trigger generation module 136 can begin generating a transaction trigger data structure 136a after it is determined that a satisfactory number of responses to a survey have been received. In some implementations, an explicit instruction can be provided to the transaction trigger generation module 136 from the survey aggregation module 135 that instructions the transaction trigger generation module to generate the transaction trigger data structure. In other implementations, the transaction trigger generation module 136 can detect that it is appropriate to generate the transaction trigger data structure 136a. For example, in some implementations, the transaction trigger generation module 136 may detect a changing state of a flag (e.g., flag changing from "0" to "1" or from "1" to "0"), and then the transaction trigger generation module 136 can begin generation of the transaction trigger record based on the detection of the toggled flag. By way of example, the transaction trigger generation module 136 can detect the toggling of a flag to a state indicating that a satisfactory number of response have been received. In such instances, the transaction trigger generation module can begin generation a transaction trigger record based on a cluster of received responses.

The transaction trigger generation module 136 can generate a transaction trigger record 136a based on the response. A transaction trigger record can be a data structure having one or more fields structuring data that includes data indicating one or more particular report dates that relate to the survey response data, indicates one or more report identifiers, and data describing, for each report identifier, a distribution list of one or more recipients that is logically related to the particular report identifier, and triggering logic. In some instances, the aforementioned data included in the transaction trigger record can be derived from the survey response data. In other implementations, the aforementioned data included in the transaction trigger record can be obtained by first accessing data within the response data and then using the access data to obtain the aforementioned data. For example, the transaction trigger generation module 136 can access information in each survey response such as (i) a response originator and (ii) a survey identifier. Then, the transaction trigger generation module 136 can search one or more other database to obtain information that describes a report distribution list for the survey response originator and (ii) a type and frequency of report based on the survey, answers to the survey, or both. In some implementations, the transaction trigger generation module 136 can obtain information using one of these methods, both of these methods, one or more of these methods and other methods, or the like. In some implementations, a transaction trigger record 136*a* is generated for each survey response 140-1*a*, 140-2*a*, 140-*na*. However, in other implementations, a transaction trigger record 136*a* may be generated for less than all of the survey responses 140-1*a*, 140-2*a*, 140-*na*.

For example, in some implementations, a subset of the computers 140-1, 140-2, 140-*n* may be associated with a single enterprise, organization, or the like. In such instances, it may not be necessary to generate a transaction trigger record 136*a* that can be added to a calendar application of multiple entities at the same organization. For example, in an implementation multiple managers of a company that are resident in multiple different geographic locations may receive an electronic message 134*a* with reference to a survey. Such wide casting of the electronic message 134*a* with a reference to the survey may be achieved in order to ensure at least one person at the company receives and responds to the survey. In some instances, even if multiple people may respond to the survey from the same company, it may not be necessary for each respondent to receive a report based on the survey. In some implementations, for example, the survey can even include a question prompting for a name (or other identifier) of a person at the company that should receive the report. In such an implementation, it may only be required to generate a transaction trigger generation module 135 to generate a transaction trigger record 136*a* for the company that is sent to the name identified in the survey instead of generating a transaction trigger record for each survey response 140-1, 140-2, 140-*n*. Even though a single transaction trigger record 136*a* may be generated for a company, the transaction trigger record 136*a* generation process may still consider answer to survey items in generation of the transaction trigger record 136*a*. nonetheless, significant savings in resources expended and reduction in latency can be achieved by reducing the number of transaction trigger records 136*a* that need to be generated for a company. Though an example of using a name in a survey to reduce the number of transaction trigger records 136*a* that need to be generated is provided, the present disclosure need not be so limited. Instead, other methods such as looking up a key contact or primary contact for the company in a directory maintained by, or otherwise accessible to, the application serve 130 may also be used to identify a person from a company for which the transaction trigger record should be directed.

The transaction trigger record 136*a* can be made accessible to the calendar API 137 for integration with a customer, client, or other person's calendar application. In some implementations, the transaction trigger generation module 136 provides the transaction trigger record 136*a* as an input parameter to the calendar API 137. In other implementations, the calendar API can detect that the transaction trigger record 136*a* has been generated based on, for example, the toggling of a flag, for example, from "0" to "1" or from "1" to "0." Then, based upon the detection of the generated transaction trigger record 136*a*, the calendar API 137 can access the transaction trigger record 136*a* from its memory location and begin the process of integrating the transaction trigger record 136*a* into its corresponding calendar application.

In some implementations, the calendar API 137 is configured so as to directly access and modify a person's personal calendar application 112, 152, or both 112 and 152. A calendar application can include an iOS calendar, a Google Calendar, or any other personal calendar or productivity application that can function to track the date of record or data entry. In some implementations, the personal calendar may be a local application 112 on a person's user device 110. In some implementations, the personal calendar may include a cloud-based calendar application hosted on a cloud-based server 150 that is remote from the user's device 110. In some implementations, the user's personal calendar may maintained both locally and in the cloud.

To obtain access to the user's personal calendar 112, 152, or 112 and 152, a user of the user device 110 may need create an account that is associated with the calendar API 137 and provide access credentials to the calendar API 137. For example, the application server 130 may offer a customer or client portal where a user of the user device 110 can sign up for the service of integrating transaction trigger records 136*a* into the user's personal calendar 112, 152, or both 112 and 152. In other implementations, the user device 110 may already have one or more software applications installed by an employer that provides calendar API 137 with access to calendar application 112, 152, or 112 and 152.

The calendar API 137 can generated a calendar update notification 137*a* that includes a version of the transaction trigger record 136*a* that has been formatted for a particular person's calendar application 112, 152, or 112 and 152. This can include, for example, determining by the calendar API 137 whether the transaction trigger record 136*a* is destined for a Apple device, an Android device, or other type of device, and then formatting the transaction trigger 136*a* into a calendar update notification 137*a* that, when processed by a receiving computer such as the user device 110 and or the cloud-based server 150, cause the receiving computer to install the transaction trigger record 136*a* of the calendar updater notification 137*a* as an entry in the personal calendar of a particular user that is to receive reports generated by the system. The application server 130 can use the calendar API 137 to interface with the personal calendar application 112, 152, or 112 and 152 and communicate the calendar update notification 137*a* to the user device 110 (option A), cloud-server 150 (option B), or both, for use in updating the personal calendar of the user. In some implementations, the application server 130 can be configured to transmit the calendar update notification 137*a* to the cloud-server 150, which updates the cloud-server calendar 152 and then pushes an update 152 to the local calendar of the user device 110. Communications between the application server 130 and the user device 110, the cloud-based server, as well as, the communications between the cloud-base server 150 and the user device 100 may achieved using the network 122. In some implementations, the network 122 may be the same network as the network 120. In other implementations, it may be separate network that is comprised of one or more wired Ethernet networks, one or more wireless WiFi networks, one or more optical networks, one or more cellular networks, the Internet, or any combinations thereof. Updating the personal calendar of the user can include integrating the transaction trigger record into a date entry of the personal calendar that corresponds to the date the transaction trigger record is to be triggered.

In more detail, the transaction trigger 136a that is provided used to update the user's personal calendar can include a number of different features including, but not limited to, triggering logic. The triggering logic can include program code, one or more function calls, a hyperlink that references a storage location with program code or one or more function calls, or a combination thereof. The triggering logic can be trigger on a particular date with which the transaction trigger logic is associated with. Once triggered, the transaction trigger logic can execute cause generation of one or more reports having a report identifier specified by the transaction trigger record. In some implementations, a user device 110 can have report generation software that is installed locally on the user device 110. In such instances, triggering of the transaction trigger record can include the user device 110 or the cloud-based server 105 processing the trigger logic, without user interaction, and instructing the report generation software to generate the reports identified by the transaction trigger record.

In other implementations, the processing of the transaction trigger record 136a by the user device 110 or cloud-based 150 can cause the user device 110 or cloud-based server 150 to instruct a device that is remote from the user device 110. For example, in some implementations, the user device 110 can process the transaction trigger record 136a, without user interaction, and call programmed logic such as one or more program function calls of the transaction trigger record in order to begin generation of the one or more reports generated by a remote server. In other implementations, the program logic can include program logic, that when executed, causes accessing and dereferencing of a link to network location storing additional program logic. For example, in some implementations, the processing of the transaction trigger record 136a, without user interaction, can cause the user device 110 or the cloud-based computer 105 to access the link stored in the transaction trigger record. In such instances, the accessing of the link can trigger execution of other report generation program logic at the network location identified by the link. In such implementations, the accessing and executing the program logic at the link to cause report generation can be achieved without user interaction. The remote server can be the application server 130 or some other server. Once generated, the report can be provided for display on the user device 110 for output.

In other implementations, the programmed logic of the transaction trigger record 136a can cause generation of a report locally on the user device 110 or server 150 without relying on the application server 130 to generate the report. In some implementations, the program logic of the transaction trigger record 136a can, itself, be software program code that, when executed, functions as a report generation module and can generate the report specified by the identifier of the transaction trigger record 136a. In other implementations, the program logic of a transaction trigger record 136a can point to a storage location on the user device 110 or server 150 that stores program code that, when executed causes generation of a report.

In any of the scenarios identified above, the transaction trigger record 136a can be integrated with a calendar application 112, 152, or 112 and 152. This integration can occur by the Calendar API 137 integrating the transaction trigger record 136a into a date entry of the calendar application 112, 152, or 112 and 152. In implementations of the present disclosure, the transaction trigger record 136a can include a data structure has fields organizing (i) all data necessary for generating a report or causing generation of the report, (ii) a reference to data necessary for generating a report or causing generation of the report, (iii) or a combination thereof. Such data can include a report identifier, one or more identifiers storing a storage location storing report templates, one or more identifiers specifying storage locations storing data required to populate fields of a report identified by the report identifier and having fields specified by a report template, a date the report is to be generated, a program logic that, when executed by a computer, causes the computer to generated the report specified by the transaction trigger record, the like, or any combination thereof.

Figure 2:
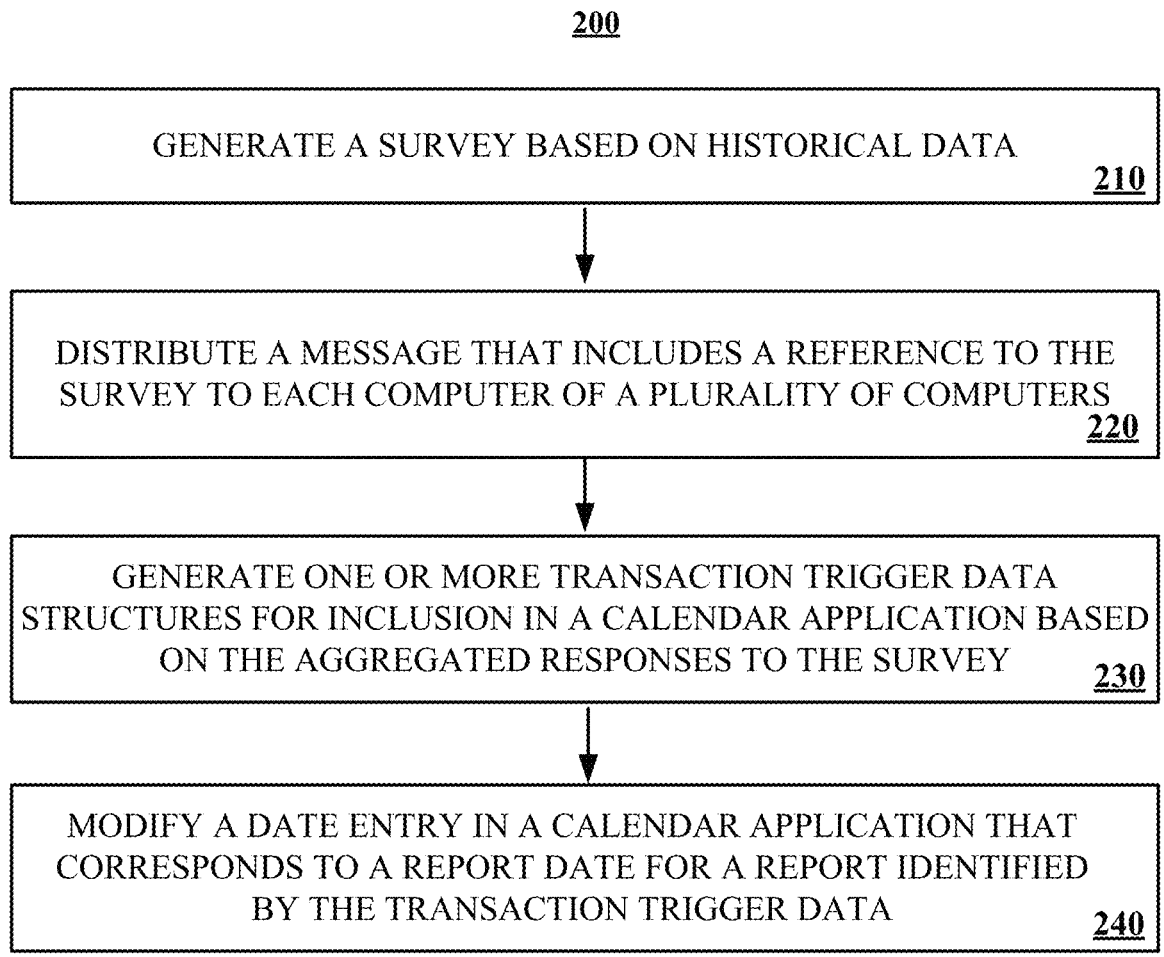
FIG. 2 is a flowchart of an example of a process for generating transaction trigger data structures.

FIG. 2 is a flowchart 200 of an example of a process for generating transaction trigger data structures. In general, the process 200 can include generating a survey based on historical data (210), distributing a message that includes a reference to the survey to each computer of a plurality of computers (220), generating one or more transaction trigger data structures for inclusion in a calendar application based on the aggregated responses to the survey (230), and modifying a date entry in a calendar application that corresponds to a report date for a report identified by the transaction trigger record (240).

Variations of the process 200 also fall within the scope of the present disclosure. For example, in some implementations, at a point in time after the generation of the transaction trigger record in stage 230 and modification of the calendar entry in stage 240, the process 200 can also include detecting, based on (i) data identifying a current date and (ii) the transaction trigger data structure stored in the calendar application, that the transaction trigger data structure is to be triggered. Based on a determination that the transaction trigger data structure is to be triggered, execution of the process 200 can further include executing the triggering logic of the transaction trigger data structure.

In some implementation, executing the triggering logic of the transaction trigger data structure can include for each report identifier of the transaction trigger record: generating, by the one or more computers, a report data structure that includes fields structuring data representing a particular report type that is identified by the report identifier, and distributing, by the one or more computers, the report data structure to a computer that is associated with each recipient of the distribution list that is logically related to the report identifier for which the report was generated.

The survey of stage 210 can be implemented in a number of different was. For example, in some implementations, the process the generated survey can include a web form that is accessible via one or more networks. In some implementations, the reference to the survey included in the transaction trigger record can include a hyperlink.

In some implementations, the transaction trigger record can include a data structure having fields structuring data that includes triggering logic. In some implementations, the triggering logic can include programmed code that, when executed, causes the computer to: for each report identifier of the transaction trigger record: generate a report data structure that includes fields structuring data representing a particular report type that is identified by the report identifier, and distribute the report data structure to a computer that is associated with each recipient of the distribution list that is logically related to the report identifier for which the report was generated.

In some implementations, the triggering logic can include computer executable program code that causes the computer to perform the operations of (i) generating the report data structure and (ii) distributing the report data structure. In other implementations, triggering logic can include a reference to a memory location storing the computer executable program code that causes the computer to perform the operations of (i) generating the report data structure and (ii) distributing the report data structure.

In some implementations, the process 200 can include distributions of reminder messages that remind a user to complete a survey. In some implementations, generation and transmission of such reminders can include determining, based on a difference between (i) data identifying a current date and (ii) data describing a date of a calendar entry that has been modified to include a second transaction trigger record. Then, based on determining that the difference satisfies a predetermined threshold, the process can further include for each second report identifier of the second transaction trigger record: distributing a message including a reminder related to a report identified by the second report identifier to each recipient of a distribution list that is logically related to the second report identifier.

Figure 3:
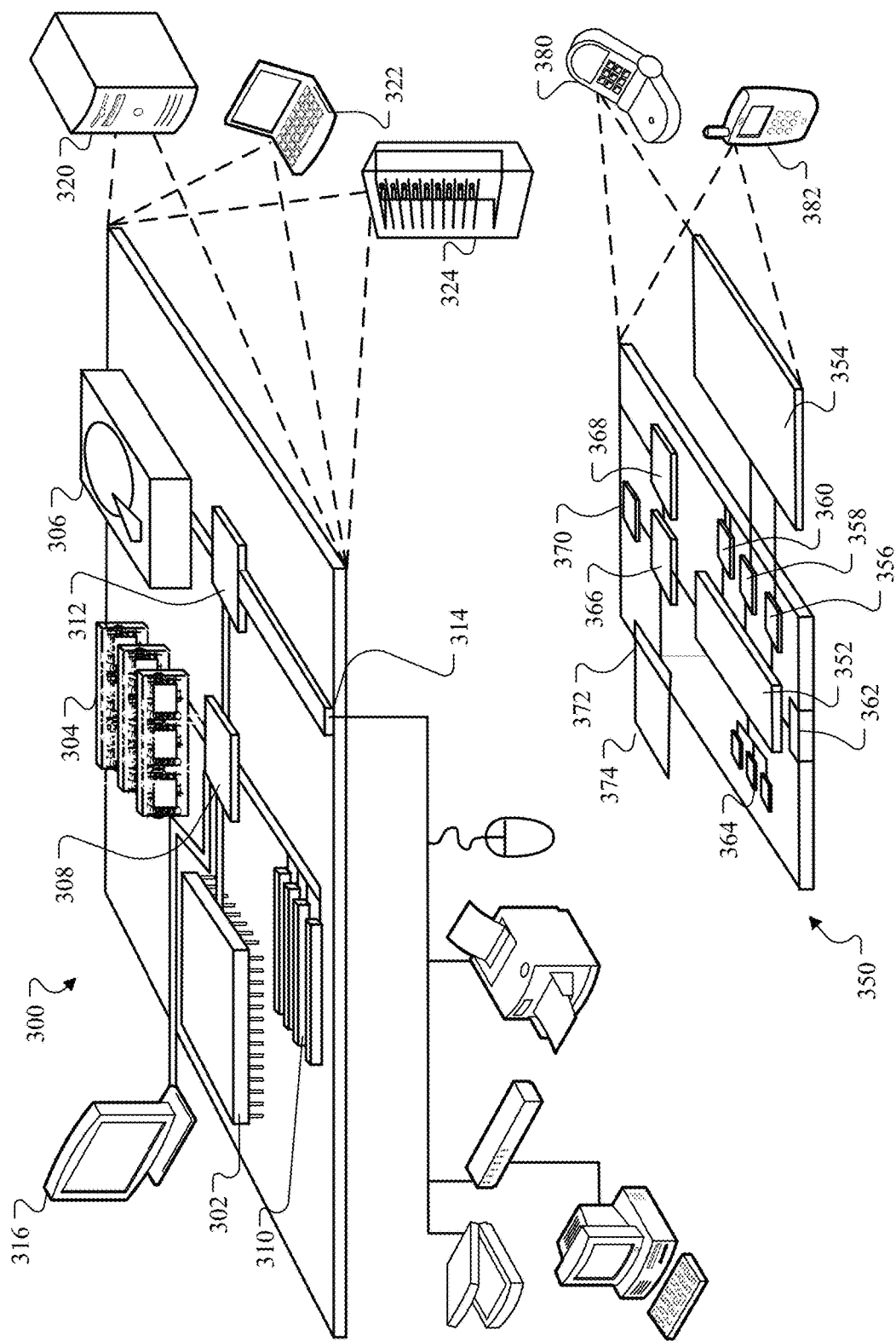
FIG. 3 is a block diagram of system components that can be used to generate transaction trigger data structures for aggregated reporting.

FIG. 3 is a block diagram of system components that can be used to generate transaction trigger data structures for aggregated reporting.

Computing device 300 is intended to represent various forms of digital computers, such as laptops, desktops, workstations, personal digital assistants, servers, blade servers, mainframes, and other appropriate computers. Computing device 350 is intended to represent various forms of mobile devices, such as personal digital assistants, cellular telephones, smartphones, and other similar computing devices. Additionally, computing device 300 or 350 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 300 includes a processor 302, memory 304, a storage device 306, a high-speed interface 308 connecting to memory 304 and high-speed expansion ports 310, and a low speed interface 312 connecting to low speed bus 314 and storage device 306. Each of the components 302, 304, 306, 308, 310, and 312, are interconnected using various busses, and can be mounted on a common motherboard or in other manners as appropriate. The processor 302 can process instructions for execution within the computing device 300, including instructions stored in the memory 304 or on the storage device 306 to display graphical information for a GUI on an external input/output device, such as display 316 coupled to high speed interface 308. In other implementations, multiple processors and/or multiple buses can be used, as appropriate, along with multiple memories and types of memory. Also, multiple computing devices 300 can be connected, with each device providing portions of the necessary operations, e.g., as a server bank, a group of blade servers, or a multi-processor system.

The memory 304 stores information within the computing device 300. In one implementation, the memory 304 is a volatile memory unit or units. In another implementation, the memory 304 is a non-volatile memory unit or units. The memory 304 can also be another form of computer-readable medium, such as a magnetic or optical disk.

The storage device 306 is capable of providing mass storage for the computing device 300. In one implementation, the storage device 306 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 304, the storage device 306, or memory on processor 302.

The high speed controller 308 manages bandwidth-intensive operations for the computing device 300, while the low speed controller 312 manages lower bandwidth intensive operations. Such allocation of functions is exemplary only. In one implementation, the high-speed controller 308 is coupled to memory 304, display 316, e.g., through a graphics processor or accelerator, and to high-speed expansion ports 310, which can accept various expansion cards (not shown). In the implementation, low-speed controller 312 is coupled to storage device 306 and low-speed expansion port 314. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 300 can be implemented in a number of different forms, as shown in the figure. For example, it can be implemented as a standard server 320, or multiple times in a group of such servers. It can also be implemented as part of a rack server system 324. In addition, it can be implemented in a personal computer such as a laptop computer 322. Alternatively, components from computing device 300 can be combined with other components in a mobile device (not shown), such as device 350. Each of such devices can contain one or more of computing device 300, 350, and an entire system can be made up of multiple computing devices 300, 350 communicating with each other.

The computing device 300 can be implemented in a number of different forms, as shown in the figure. For example, it can be implemented as a standard server 320, or multiple times in a group of such servers. It can also be implemented as part of a rack server system 324. In addition, it can be implemented in a personal computer such as a laptop computer 322. Alternatively, components from computing device 300 can be combined with other components in a mobile device (not shown), such as device 350. Each of such devices can contain one or more of computing device 300, 350, and an entire system can be made up of multiple computing devices 300, 350 communicating with each other.

Computing device 350 includes a processor 352, memory 364, and an input/output device such as a display 354, a communication interface 366, and a transceiver 368, among other components. The device 350 can also be provided with a storage device, such as a micro-drive or other device, to provide additional storage. Each of the components 350, 352, 364, 354, 366, and 368, are interconnected using various buses, and several of the components can be mounted on a common motherboard or in other manners as appropriate.

The processor 352 can execute instructions within the computing device 350, including instructions stored in the memory 364. The processor can be implemented as a chipset of chips that include separate and multiple analog and digital processors. Additionally, the processor can be implemented using any of a number of architectures. For example, the processor 310 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 350, such as control of user interfaces, applications run by device 350, and wireless communication by device 350.

Processor 352 can communicate with a user through control interface 358 and display interface 356 coupled to a display 354. The display 354 can be, for example, a TFT (Thin-Film-Transistor Liquid Crystal Display) display or an OLED (Organic Light Emitting Diode) display, or other appropriate display technology. The display interface 356 can comprise appropriate circuitry for driving the display 354 to present graphical and other information to a user. The control interface 358 can receive commands from a user and convert them for submission to the processor 352. In addition, an external interface 362 can be provide in communication with processor 352, so as to enable near area communication of device 350 with other devices. External interface 362 can provide, for example, for wired communication in some implementations, or for wireless communication in other implementations, and multiple interfaces can also be used.

The memory 364 stores information within the computing device 350. The memory 364 can be implemented as one or more of a computer-readable medium or media, a volatile memory unit or units, or a non-volatile memory unit or units. Expansion memory 374 can also be provided and connected to device 350 through expansion interface 372, which can include, for example, a SIMM (Single In Line Memory Module) card interface. Such expansion memory 374 can provide extra storage space for device 350, or can also store applications or other information for device 350. Specifically, expansion memory 374 can include instructions to carry out or supplement the processes described above, and can include secure information also. Thus, for example, expansion memory 374 can be provide as a security module for device 350, and can be programmed with instructions that permit secure use of device 350. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 364, expansion memory 374, or memory on processor 352 that can be received, for example, over transceiver 368 or external interface 362.

Device 350 can communicate wirelessly through communication interface 366, which can include digital signal processing circuitry where necessary. Communication interface 366 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 368. In addition, short-range communication can occur, such as using a Bluetooth, Wi-Fi, or other such transceiver (not shown). In addition, GPS (Global Positioning System) receiver module 370 can provide additional navigation- and location-related wireless data to device 350, which can be used as appropriate by applications running on device 350.

Device 350 can also communicate audibly using audio codec 360, which can receive spoken information from a user and convert it to usable digital information. Audio codec 360 can likewise generate audible sound for a user, such as through a speaker, e.g., in a handset of device 350. Such sound can include sound from voice telephone calls, can include recorded sound, e.g., voice messages, music files, etc. and can also include sound generated by applications operating on device 350.

The computing device 350 can be implemented in a number of different forms, as shown in the figure. For example, it can be implemented as a cellular telephone 380. It can also be implemented as part of a smartphone 382, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A method for generating transaction trigger data structures for aggregated reporting, comprising:
generating, by one or more computers, a survey based on historical data;
distributing, by the one or more computers, a message that includes a reference to the survey to each computer of a plurality of computers;
aggregating, by the one or more computers and using a data structure having fields structuring data corresponding to question-answer pairs of the survey, responses to the survey from each of the plurality of computers;
generating, by the one or more computers, one or more transaction trigger data structures that program a calendar application with one or more fields structuring data based on the aggregated responses to the survey and a particular date, wherein each transaction trigger data structure:
(i) includes the particular date; and
(ii) includes the one or more fields structuring data that:
indicates one or more report identifiers,
indicates, for each particular report identifier of the one or more report identifiers, a distribution list of one or more recipients that is logically related to the particular report identifier,
includes data including at least the responses to the surveys and a link to the responses to the surveys, and
includes triggering logic comprising program code that, when triggered, and executed by the one or more computers or a computer hosting a calendar application, programs the one or more computers or the computer hosting the calendar application to, responsive to a determination that a calendar-based trigger has been met, automatically without user interaction cause the one or more computers or the computer hosting the calendar application to dereference a link to a network location to obtain additional program logic that is executed to generate a report, for display at the computer hosting the calendar application, based on the data including at least the responses to the surveys and the executed additional program logic obtained via the dereferenced link;
modifying, by the one or more computers, a date entry in a calendar application corresponding to the particular date to include the transaction trigger data structure associated with the particular date.

2. The method of claim 1, the method further comprising:
subsequent to generating the one or more transaction trigger data structures and modification of the data entry in the calendar application:
detecting, by the one or more computers and based on (i) data identifying a current date and (ii) the transaction trigger data structure stored in the calendar application, that the transaction trigger data structure is to be triggered; and
executing, by the one or more computers, the triggering logic of the transaction trigger data structure, wherein execution of the triggering logic of the transaction trigger data structure causes the one or more computers or the computer hosting the calendar application to:
for each report identifier of the transaction trigger data structure:
generate a report data structure that includes fields structuring data representing a particular report type that is identified by the report identifier; and
distribute the report data structure to a computer that is associated with each recipient of the distribution list that is logically related to the report identifier for which the report was generated.

3. The method of claim 1, wherein the reference to the survey includes a hyperlink.

4. The method of claim 1, wherein the triggering logic includes computer programmed code that, when executed, causes the one or more computers or the computer hosting the calendar application to:
for each report identifier of the transaction trigger data structure:
generate a report data structure that includes fields structuring data representing a particular report type that is identified by the report identifier; and
distribute the report data structure to a computer that is associated with each recipient of the distribution list that is logically related to the report identifier for which the report was generated.

5. The method of claim 1, wherein data identifying the triggering logic includes computer executable program code that causes the one or more computers or the computer hosting the calendar application to (i) generate the report data structure and (ii) distribute the report data structure.

6. The method of claim 1, the method further comprising:
determining, by the one or more computers, a difference between (i) data identifying a current date and (ii) data describing a date of a calendar entry that has been modified to include a second transaction trigger data structure; and
determining that the difference satisfies a predetermined threshold; and
responsive to determining that the difference satisfies the predetermined threshold:
for each second report identifier of the second transaction trigger data structure:
distributing a message that includes a reminder related to a report identified by the second report identifier to each recipient of a distribution list that is logically related to the second report identifier.

7. A system for generating transaction trigger data structures for aggregated reporting, the system comprising:
one or more computers; and
one or more computer-readable storage media storing instructions that, when executed by the one or more computers, cause the one or more computers to:
generate a survey based on historical data;
distribute a message that includes a reference to the survey to each computer of a plurality of computers;
aggregate, using a data structure having fields structuring data corresponding to question-answer pairs of the survey, responses to the survey from each of the plurality of computers;
generate one or more transaction trigger data structures that program a calendar application with one or more fields structuring data based on the aggregated responses to the survey and a particular date, wherein each transaction trigger data structure (i) includes the particular date and (ii) includes the one or more fields structuring data that (a) indicates one or more report identifiers, (b) indicates, for each particular report identifier of the one or more report identifiers, a distribution list of one or more recipients that is logically related to the particular report identifier, and (c) includes triggering logic comprising program code that, when triggered, and executed by the one or more computers or a computer hosting a calendar application, programs the one or more computers or the computer hosting the calendar application to, responsive to a determination that a calendar-based trigger has been met, automatically without user interaction cause the one or more computers or the computer hosting the calendar application to dereference a link to a network location to obtain additional program logic that is executed to generate a report, for display at the computer hosting the calendar application, based on the data including at least the responses to the surveys and the executed additional program logic obtained via the dereferenced link; and
modify a date entry in a calendar application corresponding to the particular date to include the transaction trigger data structure associated with the particular date.

8. The system of claim 7, wherein the instructions further cause the one or more computers to:
subsequent to generation of the one or more transaction trigger data structures and modification of the data entry in the calendar application:
detect, based on (i) data identifying a current date and (ii) the transaction trigger data structure stored in the calendar application, that the transaction trigger data structure is to be triggered; and
execute the triggering logic of the transaction trigger data structure, wherein execution of the triggering logic of the transaction trigger data structure causes the one or more computers to:
for each report identifier of the transaction trigger data structure:
generate a report data structure that includes fields structuring data representing a particular report type that is identified by the report identifier; and
distribute the report data structure to a computer that is associated with each recipient of the distribution list that is logically related to the report identifier for which the report was generated.

9. The system of claim 8, wherein to execute the triggering logic of the transaction trigger data structure, the one or more computers or the computer hosting the calendar application are further caused to: obtain the computer executable program code that causes the one or more computers or the computer hosting the calendar application to: (i) generate the report data structure and (ii) distribute the report data structure.

10. The system of claim 7, wherein the generated survey includes a web form that is accessible via one or more networks.

11. The system of claim 7, wherein the reference to the survey includes a hyperlink.

12. The system of claim 7, wherein the triggering logic includes computer programmed code that, when executed, causes the one or more computers or the computer hosting the calendar application to:
for each report identifier of the transaction trigger data structure:
generate a report data structure that includes fields structuring data representing a particular report type that is identified by the report identifier; and
distribute the report data structure to a computer that is associated with each recipient of the distribution list that is logically related to the report identifier for which the report was generated.

13. The system of claim 7, wherein data identifying the triggering logic includes computer executable program code that causes the one or more computers to: (i) generate the report data structure and (ii) distribute the report data structure.

14. The system of claim 7, wherein data identifying the triggering logic includes a reference to a memory location storing the computer executable program code that causes the one or more computers to: (i) generate the report data structure and (ii) distribute the report data structure.

15. The system of claim 7, wherein the one or more computers are further caused to:
determine a difference between (i) data identifying a current date and (ii) data describing a date of a calendar entry that has been modified to include a second transaction trigger data structure; and
determine that the difference satisfies a predetermined threshold;
responsive to the determination that the difference satisfies the predetermined threshold:
for each second report identifier of the second transaction trigger data structure:
distribute a message that includes a reminder related to a report identified by the second report identifier to each recipient of a distribution list that is logically related to the second report identifier.

16. A non-transitory computer-readable medium storing software comprising instructions executable by one or more computers which, upon such execution, cause the one or more computers to:
generate a survey based on historical data;
distribute a message that includes a reference to the survey to each computer of a plurality of computers;
aggregate, using a data structure having fields structuring data corresponding to question-answer pairs of the survey, responses to the survey from each of the plurality of computers;
generate one or more transaction trigger data structures that program a calendar application with one or more fields structuring data based on the aggregated responses to the survey and a particular date, wherein each transaction trigger data structure (i) includes the particular date and (ii) includes the one or more fields structuring data that (a) indicates one or more report identifiers, (b) indicates, for each particular report identifier of the one or more report identifiers, a distribution list of one or more recipients that is logically related to the particular report identifier, and (c) includes triggering logic comprising program code that, when triggered, and executed by the one or more computers or a computer hosting a calendar application, programs the one or more computers or the computer hosting the calendar application to, responsive to a determination that a calendar-based trigger has been met, automatically without user interaction cause the one or more computers or the computer hosting the calendar application to dereference a link to a network location to obtain additional program logic that is executed to generate a report, for display at the computer hosting the calendar application, based on the data including at least the responses to the surveys and the executed additional program logic obtained via the dereferenced link; and modify a date entry in a calendar application corresponding to the particular date to include the transaction trigger data structure.

17. The computer-readable medium of claim 16, the instructions further causing the one or more computers to:
subsequent to generation of the transaction trigger data structure and modification of the data entry in the calendar application:
detect, based on (i) data identifying a current date and (ii) the transaction trigger data structure stored in the calendar application, that the transaction trigger data structure is to be triggered; and
execute the triggering logic of the transaction trigger data structure, wherein execution of the triggering logic of the transaction trigger data structure causes the one or more computers or the computer hosting the calendar application to:
for each report identifier of the transaction trigger data structure:
generate a report data structure that includes fields structuring data representing a particular report type that is identified by the report identifier; and
distribute the report data structure to a computer that is associated with each recipient of the distribution list that is logically related to the report identifier for which the report was generated.

18. The computer-readable medium of claim 16, wherein the triggering logic includes computer programmed code that, when executed, causes the one or more computers or the computer hosting the calendar application to:
for each report identifier of the transaction trigger data structure:
generate a report data structure that includes fields structuring data representing a particular report type that is identified by the report identifier; and
distribute, by the one or more computers, the report data structure to a computer that is associated with each recipient of the distribution list that is logically related to the report identifier for which the report was generated.

19. The computer-readable medium of claim 16, wherein data identifying the triggering logic includes computer executable program code that causes the one or more computers or the computer hosting the calendar application to: (i) generate the report data structure and (ii) distribute the report data structure.

20. The computer-readable medium of claim 16, wherein the instructions further cause the one or more computers to:
determine a difference between (i) data identifying a current date and (ii) data describing a date of a calendar entry that has been modified to include a second transaction trigger data structure; and
determine that the difference satisfies a predetermined threshold; and
responsive to the determination that the difference satisfies the predetermined threshold:
for each second report identifier of the second transaction trigger data structure:
distribute a message that includes a reminder related to a report identified by the second report identifier to each recipient of a distribution list that is logically related to the second report identifier.

* * * * *